(12) United States Patent
Thomas et al.

(10) Patent No.: US 8,337,595 B2
(45) Date of Patent: Dec. 25, 2012

(54) PURIFICATION OF TRANS-1,3,3,3-TETRAFLUOROPROPENE

(75) Inventors: Raymond Hilton Thomas, Pendleton, NY (US); Stephen A. Cottrell, Churchville, NY (US)

(73) Assignee: Honeywell International Inc., Morristown, NJ (US)

( * ) Notice: Subject to any disclaimer, the term of this patent is extended or adjusted under 35 U.S.C. 154(b) by 104 days.

(21) Appl. No.: 13/090,550

(22) Filed: Apr. 20, 2011

(65) Prior Publication Data

US 2012/0266750 A1   Oct. 25, 2012

(51) Int. Cl.
*B01D 53/02* (2006.01)
(52) U.S. Cl. ............................................ 95/131; 95/142
(58) Field of Classification Search ............... 95/90, 131, 95/142
See application file for complete search history.

(56) References Cited

U.S. PATENT DOCUMENTS

| 7,084,315 | B2 | 8/2006 | Corr et al. |
| 7,597,744 | B2 | 10/2009 | Thomas et al. |
| 7,803,975 | B2 | 9/2010 | Knapp |
| 2010/0185027 | A1 | 7/2010 | Wang et al. |

FOREIGN PATENT DOCUMENTS

JP    2010083818 A   4/2010

*Primary Examiner* — Duane Smith
*Assistant Examiner* — Christopher P Jones
(74) *Attorney, Agent, or Firm* — Bruce O. Bradford

(57) ABSTRACT

Disclosed is a process for removing impurities from a product stream comprising trans HFO-1234ze and an HFO-1234 impurity that uses one or more adsorbents that are selective for the HFO-1234 impurity, such that the HFO-1234 impurity is removed from the product stream. One such impurity is HFO-1234zc, which is removed from its mixture with trans HFO-1234ze by action of an adsorbent having pores in the range of from about 5 angstroms to about 10 angstroms.

19 Claims, No Drawings

PURIFICATION OF TRANS-1,3,3,3-TETRAFLUOROPROPENE

BACKGROUND OF THE INVENTION

There is great concern about climate change that is driven by the use of man made materials. Refrigerants, solvents and blowing agents have been identified as a class of materials that have a high potential for contributing to climate change. This is because materials previously used in these applications have been a class of compounds whose atmospheric life is long enough to increase global warming and/or ozone depletion.

A new class of compounds has been discovered as replacements for the former compounds. This class of compounds is generically known as hydrofluoroolefins (HFOs). HFOs are suitable for use as refrigerants, solvents and blowing agents and have short atmospheric lifetimes. The lifetimes are such that they are minimal contributors to global warming and/or ozone depletion, and these compounds can meet the guidelines being proposed of legislated for such applications.

Trans HFO-1234ze (trans-1,3,3,3-tetrafluoropropene) is one such material. Its global warming potential will meet all currently proposed guidelines. However, some fluoroolefins are known to be toxic or otherwise undesirable. Trans HFO-1234ze has been tested for toxicity and found to be generally non-toxic and very suitable for use as a blowing agent, refrigerant or solvent. Accordingly, the presence of other fluoroolefins, even at low concentrations, may be a cause for concern unless they have been tested for toxicity. During the production of trans HFO-1234ze, the present inventors have observed the presence of at least one other isomer of HFO-1234 ($C_3H_2F_4$), such as HFO-1234zc, whose toxicity is unknown. In view of the unknown toxicity, the desire to remove this impurity and other impurities (e.g., other HFO compounds) from the product stream was formed. These impurities are collectively referred to herein as "the HFO-1234 impurity."

There are many separation techniques that are available. Distillation is standard and very efficient means of separation. However, in cases where the volatility of the impurity is similar to that of the product, standard distillation techniques may not work. It may then be necessary to apply more complicated distillation techniques such as the use of multiple columns and even cryogenic techniques; see for example, U.S. Pat. No. 5,261,948. These techniques can be expensive and/or difficult to use. Alternatively, it would then be desirable to apply adsorptive techniques, if a suitable sorbent can be identified.

One of the means of purification of gas streams is to utilize molecular sieves. However, there are many kinds of molecular sieves with varying pore sizes. A molecular sieve is a material containing tiny pores of a precise and uniform size that is used as an adsorbent for gases and liquids. Molecules small enough to pass through the pores are adsorbed while larger molecules are not. The principle of absorption to molecular sieve particles is somewhat similar to that of size exclusion chromatography, except that without a changing solution composition, the adsorbed product remains trapped because in the absence of other molecules able to penetrate the pore and fill the space, a vacuum would be created by desorption.

Often molecular sieves consist of aluminosilicate minerals, clays, porous glasses, microporous charcoals, zeolites, active carbons, or synthetic compounds that have open structures through which small molecules can diffuse.

Separations using molecular sieves are partly dependent on the size of the molecules of the gas components. However, different means of estimating molecular sizes yield different results. This makes it impossible to be sure that a particular sieve will produce the required separation. It is also true that many important zeolite based separation processes are not based on the sieving action of the zeolite. They are instead based on the difference between the equilibrium amounts of the gas components adsorbents. See, Gas Separation by Adsorption Processes, by R. T. Yang, Butterworth Series in Chemical Engineering, 1987. Indeed it is possible that the differences in amounts of gas components adsorbed can be such as to increase the concentration of the unwanted impurity.

Another feature that can control the separation process is the kinetics of the materials to be separated. Foley at al., in U.S. Pat. No. 5,261,948, teach that oxygen and nitrogen differ in size by only 0.2 angstrom and the equilibrium loading levels of the two gases are almost identical. Nevertheless, their separation using carbon molecular sieves is efficient. This separation depends on the fact that the rate of transport of oxygen into the carbon sieve pore structure is much higher than that of nitrogen. Another factor that can affect the separation is the shape of gas molecules as compared to the shape of the opening in the adsorbent. The choice of molecular sieve as an adsorbent is therefore unobvious. The sieving material can be either a zeolite type or a carbon molecular sieve.

Methods for the regeneration of molecular sieves include pressure change, heating and purging with a carrier gas, or heating under vacuum conditions. Temperatures typically used to regenerate water-adsorbed molecular sieves typically range from 130° C. to 250° C.

SUMMARY OF THE INVENTION

In accordance with one embodiment of this invention it has been discovered that the use of molecular sieves of an acceptable effective pore size provides a process for separating trans HFO-1234ze from its mixture with other materials, particularly impurities which comprise the HFO-1234 impurity, whose molecular sieve diameters permit adsorption so as to reduce the amount of impurities in the mixture. The process may be conducted with any suitable molecular sieve and is suitable for separating trans HFO-1234ze from its mixture with any other material that has a molecular diameter, polarity, kinetics, shape, or other property such that a separation is possible.

Given the complexity of the separation process, it is very difficult to predict which molecular sieves will separate various combinations of materials. The process of this invention is particularly suitable for removing the HFO-1234 impurity from the desired compound, trans HFO-1234ze.

In accordance with one embodiment of this invention there is provided a process for trapping or separating at least a portion of the HFO-1234 impurity from its mixture with trans HFO-1234ze so as to reduce the amount of the HFO-1234 impurity in the mixture.

This process may be conducted at a temperature of from about −20° C. to 100° C. and comprises adsorbing the impurity by contacting the product stream with a solid adsorbent comprising pores having openings which have a size across their largest dimension in the range of from about 5 angstroms to about 10 angstroms.

One preferred embodiment of this invention is thus directed to a process for removing impurities from a product stream comprising trans HFO-1234ze and an HFO-1234 impurity that uses one or more adsorbents that are selective for the HFO-1234 impurity, such that the HFO-1234 impurity is removed from the product stream.

DETAILED DESCRIPTION OF THE INVENTION

As described herein, the process of the present invention is particularly suitable for removing the HFO-1234 impurity produced during the production of trans HFO-1234ze by interaction between the reaction products with a suitable adsorbent agent or combinations of such agents. The process may be conducted with any suitable molecular sieve that is suitable for separating the HFO-1234 impurity from a mixture with trans HFO-1234ze.

In a preferred embodiment, the present invention is directed to a process for removing impurities from a product stream comprising trans HFO-1234ze and an HFO-1234 impurity that uses one or more adsorbents that are selective for the HFO-1234 impurity, such that the HFO-1234 impurity is removed from the product stream. One such impurity is HFO-1234zc, which is removed from its mixture with trans HFO-1234ze by action of an adsorbent having pores in the range of from about 5 angstroms to about 10 angstroms.

While it is difficult to predict molecular sieve separations, the present inventors have found that the HFO-1234 impurity can be separated from trans HFO-1234ze by the use of molecular sieves whose pore diameters range from about 5 angstroms to about 10 angstroms. The preferred molecular sieves have a pore diameter of about 5 angstroms.

A product stream containing the HFO-1234 impurity in a mixture with trans HFO-1234ze can be brought into contact with the molecular sieve in either the liquid or gas phase, in a process that may be either a continuous or a batch process to adsorb the HFO-1234 impurity and thereby separate and remove it from the trans HFO-1234ze.

The level to which the HFO-1234 impurity is reduced is dependent upon the capacity of the molecular sieve and the equilibrium between the HFO-1234 impurity and the mixture of gases and in the molecular sieve itself. It is preferred to use as much molecular sieve as necessary to reduce the level of HFO-1234 impurity to less than about 500 ppm, preferably to level of less than about 100 ppm, and more preferably to a level of less than about 10 ppm. Most preferably, the level of the HFO-1234 impurity is undetectable, i.e., as close to "zero ppm" as possible.

The process of this invention may employ any suitable molecular sieve including, but not limited to, suitable zeolite and carbon molecular sieves. The suitable molecular sieve must have an acceptable effective pore size such as to adsorb the HFO-1234 impurity but not adsorb the trans HFO-1234ze. Surprisingly it has been discovered that 5 A molecular sieves (having an effective pore size of about 5 angstroms) will very effectively achieve the desired separation of HFO-1234 impurity from trans HFO-1234ze. Thus, it is believed that the HFO-1234 impurity has an effective molecular diameter of less than about 5 Å and that the effective molecular diameter of trans HFO-1234ze is greater than 5 angstroms. Thus, given the differences in effective molecular diameters, separation of the HFO-1234 impurity from trans HFO-1234ze can be effected by using molecular sieves whose diameters are less than the effective molecular diameter of trans HFO-1234ze.

Molecular sieves useful in the process of this invention are available from a variety of sources, including but not limited to, zeolite molecular sieves from Universal Oil Products (UOP), Grace Chemical and Aldrich Chemical Co., and carbon molecular sieves from Aldrich Chemical Co., Chemos GmbH of Germany and Dayung Chemical Co., Ltd. of China.

EXAMPLES

The present invention is illustrated by, but not limited to, the following examples. As shown below, the present inventors compared the separation of the HFO-1234 impurity from a mixture with trans HFO-1234ze using two different molecular sieves, namely 13X sieves and 5A sieves (obtained commercially from UOP and Grace Chemical). The rough size of the pores in these sieves is about 10 angstroms and about 5 angstroms, respectively. The 13X sieve reduced the level of the HFO-1234 impurity somewhat, but did not remove it entirely. The 5A sieve was surprisingly effective in removing all of the HFO-1234 impurity. Table 1 below presents the data from the experiments conducted.

TABLE 1

Examples and Comparatives

| Experiment # | Initial | 1 | 2 | 3 | 4 | 5 | 6 |
|---|---|---|---|---|---|---|---|
| Mass of Crude (g) | | 5 | 10 | 20 | 5 | 10 | 20 |
| Mass retained in sieve (g) | | 0.42 | 0.88 | 0.84 | 0.69 | 0.67 | 0.68 |
| % of sieve mass | | 8.4 | 17.6 | 16.8 | 13.80 | 13.40 | 13.60 |
| trans HFO-1234ze | 70.59 | 82.35 | 71.57 | 71.25 | 90.77 | 83.62 | 76.69 |
| HFO-1234 impurity | 0.11 | 0.000 | 0.000 | 0.000 | 0.0125 | 0.0451 | 0.0826 |

Experiments 1 to 3 are examples and use 5A molecular sieve.
Experiments 4 to 6 are comparatives and use 13X molecular sieves.

Experimental Procedure

The initial concentration of the impurity is shown in the Table to be 0.11 area % (GC). The basic is experiment is as follows: 5 grams of activated molecular sieve were put into a 40 cc cylinder. An amount (5, 10 or 20 grams) of the crude mixture (which also contains cis HFO-1234ze and HFC-245fa) was put into the cylinder containing the sieves. The cylinder was then allowed to sit at room temperature (23° C.) overnight. The gas was then removed from the cylinder using liquid nitrogen on the receiving cylinder and very gentle heating on the cylinder with the sieves. The gas was then analyzed for the undesirable HFO-1234 impurity. When the molecular sieve was 5 A, there was no undesirable HFO-1234 impurity detected. When the molecular sieve was 13X, some of the HFO-1234 impurity was still present.

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A process for removing impurities from a product stream comprising trans HFO-1234ze and an HFO-1234 impurity comprising contacting the product stream with one or more adsorbents that are selective for the HFO-1234 impurity, such that the HFO-1234 impurity is removed from the product stream; wherein the adsorbent comprises pores in which the openings to the pores have a size across their largest dimension in the range of from about 5 angstroms to about 10 angstroms.

2. The process of claim 1, wherein the HFO-1234 impurity comprises at least one other isomer of HFO-1234 ($C_3H_2F_4$).

3. The process of claim 1, wherein the HFO-1234 impurity comprises HFO-1234zc.

4. The process of claim 1, wherein the HFO-1234 impurity is removed to a remainder level in the product stream of less than about 500 ppm.

5. The process of claim 1, wherein the HFO-1234 impurity is removed to a remainder level in the product stream of less than about 100 ppm.

6. The process of claim 1, wherein the HFO-1234 impurity is removed to a remainder level in the product stream of level of less than about 10 ppm.

7. The process of claim 1, wherein the HFO-1234 impurity is removed to a remainder level in the product stream of about zero ppm.

8. The process of claim 1, wherein the adsorbent comprises 5A molecular sieves.

9. The process of claim 1, wherein the adsorbent is packed in a column and the product stream is passed over the column, such that the HFO-1234 impurity is removed by the adsorbent.

10. The process of claim 1, wherein a gas containing trans HFO-1234ze and the HFO-1234 impurity is stored in a container containing the adsorbent, for a fixed amount of time, and thereafter, the purified trans HFO-1234ze gas is removed.

11. The process of claim 1, wherein the adsorbent comprises pores in which the openings to the pores have a size across their largest dimension of about 5 angstroms.

12. The process of claim 1, wherein the adsorbent is a molecular sieve.

13. The process of claim 1, wherein the adsorbent is a zeolite.

14. The process of claim 1, wherein the adsorbent is an activated carbon.

15. A process for removing impurities from a product stream comprising trans HFO-1234ze and an HFO-1234 impurity that uses one or more adsorbents that are selective for the HFO-1234 impurity, such that the HFO-1234 impurity is removed from the product stream; wherein the impurity comprises HFO-1234zc; and wherein the adsorbent comprises pores in which the openings to the pores have a size across their largest dimension in the range of from about 5 angstroms to about 10 angstroms.

16. The process of claim 15, wherein the adsorbent comprises pores in which the openings to the pores have a size across their largest dimension of about 5 angstroms.

17. The process of claim 16, wherein the adsorbent is a molecular sieve.

18. The process of claim 16, wherein the adsorbent is a zeolite.

19. The process of claim 16, wherein the adsorbent is an activated carbon.

* * * * *